United States Patent
Ko

(10) Patent No.: US 9,562,763 B2
(45) Date of Patent: Feb. 7, 2017

(54) APPARATUS FOR INSPECTING CURVATURE

(71) Applicant: Sunmoon University Industry-University Cooperation, Asan-si (KR)

(72) Inventor: Kuk Won Ko, Seongnam-si (KR)

(73) Assignee: Sunmoon University Industry—University Cooperation, Asan-si (KR)

( * ) Notice: Subject to any disclaimer, the term of this patent is extended or adjusted under 35 U.S.C. 154(b) by 0 days.

(21) Appl. No.: 14/527,056

(22) Filed: Oct. 29, 2014

(65) Prior Publication Data

US 2016/0123896 A1 May 5, 2016

(51) Int. Cl.
| | | |
|---|---|---|
| *G02B 27/00* | (2006.01) | |
| *G01B 11/24* | (2006.01) | |
| *G01N 21/88* | (2006.01) | |
| *G01B 11/255* | (2006.01) | |

(52) U.S. Cl.
CPC ........... *G01B 11/24* (2013.01); *G01N 21/8806* (2013.01); *G01B 11/255* (2013.01); *G02B 27/00* (2013.01)

(58) Field of Classification Search
CPC .... G02B 27/0025; G01B 11/24; G01B 11/255
USPC ...................... 356/237.1–241.6, 242.1–243.8, 426–431,356/600–640
See application file for complete search history.

(56) References Cited

U.S. PATENT DOCUMENTS

| | | | | |
|---|---|---|---|---|
| 4,512,197 A | * | 4/1985 | von Gutfeld | G01N 29/2418 73/601 |
| 4,591,242 A | * | 5/1986 | Broockman | G06K 7/10871 235/457 |
| 4,652,122 A | * | 3/1987 | Zincone | G05D 1/0615 356/28.5 |
| 5,484,990 A | * | 1/1996 | Lindacher | G06K 7/10811 235/462.22 |
| 6,086,234 A | * | 7/2000 | Riser | F21V 7/04 362/327 |
| 6,575,963 B1 | * | 6/2003 | Van Saarloos | A61B 18/20 359/209.1 |
| 2004/0246473 A1 | * | 12/2004 | Hermary | G01B 11/245 356/237.1 |
| 2014/0132749 A1 | * | 5/2014 | Hartman | G06K 9/00604 348/78 |
| 2015/0059026 A1 | * | 2/2015 | Hermans | G01B 11/255 850/6 |
| 2015/0062446 A1 | * | 3/2015 | Schreiber | H04N 9/317 348/745 |

* cited by examiner

*Primary Examiner* — Tri Ton
*Assistant Examiner* — Jarreas C Underwood
(74) *Attorney, Agent, or Firm* — NSIP Law

(57) ABSTRACT

An apparatus for inspecting curvature, including: a radiation unit radiating a plurality of rays of light having different focal lengths onto a surface of an target material; and an inspection unit inspecting the surface of the target material using the rays of light reflected from the target material. The apparatus can inspect the curvature or the bending of the surface of a target material at a high speed and with high accuracy.

4 Claims, 5 Drawing Sheets

APPARATUS FOR INSPECTING CURVATURE

BACKGROUND

Field

The present invention relates to an apparatus for inspecting the curvature or the bending of the surface of a target material.

Description of Related Art

When the curvature or the bending of surfaces of plate products, such as semiconductor wafers, electronic circuit boards or steel plates, exerts a negative effect upon the performance of the products, it is required to inspect the curvature or the bending of the surfaces of such products.

In the related art, to inspect the curvature or the bending of a surface, a laser distance sensor may be used. To inspect the curvature or the bending of a surface using the laser distance sensor, laser beams are radiated onto the surface such that the laser beams reflect from the surface and are received by a measuring device. Upon receiving the reflected laser beams, the measuring device measures the distances of paths of the laser beams reflected from the surface to the measuring device. When the measured distances of the reflected laser beam paths are equal to each other, the measuring device determines that the surface of the target material is a flat surface without curvature or bending.

However, the laser distance sensor is disadvantageous in that the installation cost thereof is high and it is required to precisely control the movement of the laser distance sensor when applying the sensor over a large area. Further, when the inspection is performed using a laser distance sensor, a limited number of laser distance sensors are used, so the time required to perform the inspection is excessively long.

Korean Patent No. 0564323 discloses a technique of measuring the bending of a surface of a target material using a laser distance sensor. However, this technique cannot solve the above-mentioned problems experienced in the laser distance sensor.

The foregoing is intended merely to aid in the understanding of the background of the present invention, and is not intended to mean that the present invention falls within the purview of the related art that is already known to those skilled in the art.

DOCUMENTS OF RELATED ART (Patent Document 1) Korean Patent No. 0564323

SUMMARY

Accordingly, the present invention has been made keeping in mind the above problems occurring in the related art, and the present invention is intended to propose an apparatus for inspecting a target material at a high speed and with high accuracy to determine curvature or the bending of the material's surface.

In order to achieve the above object, according to one aspect of the present invention, there is provided an apparatus for inspecting curvature, including: a radiation unit radiating a plurality of rays of light having different focal lengths onto a surface of target material; and an inspection unit inspecting the surface of the target material using the rays of light reflected from the surface of the material.

Here, the radiation unit may include: a plurality of lenses transmitting the rays of light, wherein the rays of light transmitted by the respective lenses may have different chromatic aberrations and the different focal lengths may be formed due to a difference in the chromatic aberration.

Further, when the target material moves in an x-axial direction on an xy-plane, the radiation unit may include a plurality of lenses arrayed on the xy-plane, so the rays of light radiated onto the target material via the respective lenses may have different chromatic aberrations along the x-axial direction of the lens array and the focal lengths of the rays of light may become different from each other due to the difference in the chromatic aberration.

Further, when the inspection unit determines that a ray of light radiated from the radiation unit is focused on the surface of the target material, the inspection unit may determine that the focal length of the ray of light is equal to a distance between the radiation unit and the target material, and may determine a curvature of the surface of the target material by using distances determined using the focal lengths of the rays of light.

Further, the radiation unit may include: a light source producing light; a micro lens array (MLA) that forms a plurality of light ray focal points in a direction toward the target material; and an expansion lens that expands the area formed by the focal points of the rays of light output from the MLA to a second area that is larger than a planar first area of the MLA, wherein the expansion lens may include a telecentric lens.

In another aspect, the present invention provides an apparatus for inspecting curvature, including: a light source producing white light; a first lens unit changing a path of the white light radially emitted from the light source into a rectilinear path; a spectral unit converting the white light output from the first lens unit into a plurality of fine rays of light having different chromatic aberrations and outputting the fine rays of light; a path changing unit transmitting the fine rays of light to different positions in the x-axial direction on the xy-plane; and a second lens unit forming focal points of the fine rays of light and moving in the x-axial direction relative to the target material placed on the xy-plane.

Here, the path changing unit may transmit the fine rays of light onto the xy-plane, and the chromatic aberrations of the fine rays of light transmitted to x, y positions having the same x-axial coordinates may be equal to each other.

In the apparatus for inspecting curvature, the inspection unit may receive the rays of light reflected from the target material and may determine the distance between the path changing unit or the second lens unit and the surface of the target material, wherein the path changing unit may transmit the rays of light reflected from the target material onto the inspection unit.

Further, the apparatus for inspecting curvature may further include: a third lens unit placed between the second lens unit and the target material and increasing distances between the focal points formed by the second lens unit on the xy-plane.

The apparatus for inspecting curvature of the present invention may form a plurality of light ray focal points having different focal lengths using fine rays of light having different chromatic aberrations.

As described above, the apparatus for inspecting curvature of the present invention can form a plurality of light ray focal points having different focal lengths using fine rays of light having different chromatic aberrations, and can inspect the curvature or the bending of a surface of a target material using the focal lengths at a high speed and with high accuracy.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION

Figure 1:
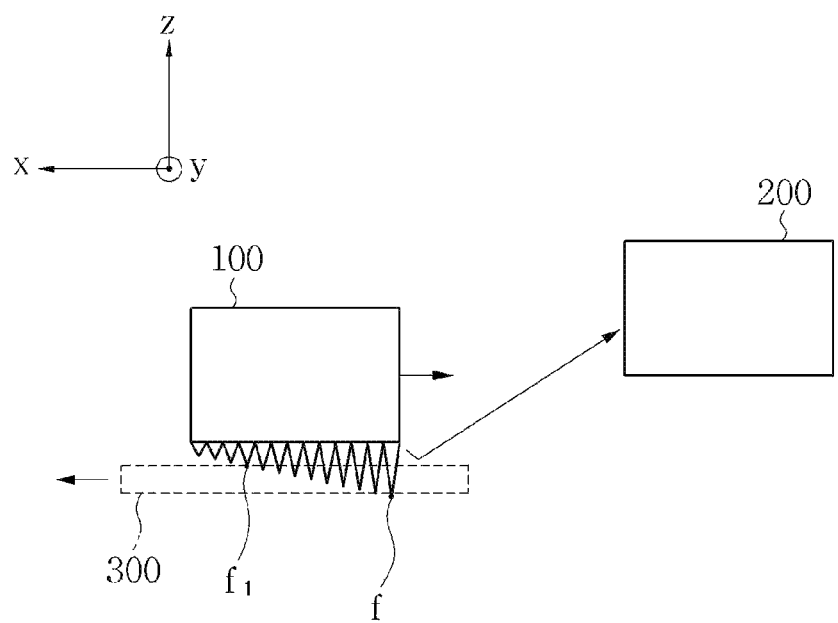
FIG. 1 is a view schematically illustrating an apparatus for inspecting curvature according to an embodiment of the present invention.

Hereinbelow, exemplary embodiments of the present invention will be described in detail with reference to the accompanying drawings. In the following description, it should be understood that the shape and size of the elements shown in the drawings may be exaggerated to provide an easily understood description of the structure of the present invention. Further, the terminologies or words used in the description and the claims of the present invention should not be interpreted as being limited merely to their common and dictionary meanings. On the contrary, they should be interpreted based on the meanings and concepts of the invention in keeping with the scope of the invention based on the principle that the inventor(s) can appropriately define the terms in order to describe the invention in the best way.

FIG. 1 is a view schematically illustrating an apparatus for inspecting curvature according to an embodiment of the present invention.

The apparatus for inspecting curvature shown in FIG. 1 may include a radiation unit 100 and an inspection unit 200.

The radiation unit 100 may radiate a plurality of rays of light having different focal lengths onto a surface of a target material 300.

The target material 300 is a material onto which the plurality of rays of light output from the radiation unit 100 is radiated. The target material 300 may be a plate product, such as a semiconductor wafer, an electronic circuit board or a steel plate, the performance of which may be affected by the curvature or the bending of a surface thereof. To inspect the curvature or the bending of the surface of the target material 300, the apparatus for inspecting curvature of the present invention uses light. Here, the light used in the present invention may be various light having different wavelengths, for example, white light.

The radiation unit 100 may focus rays of light in a direction toward the target material 300 using lenses without simply radiating light onto the surface of the target material 300. Here, the radiation unit 100 may form a plurality of light focal points having different focal lengths. To radiate a plurality of rays of light having different focal lengths, the radiation unit 100 may use the chromatic aberration of light.

Chromatic aberration is a type of distortion occurring due to different refractive indices for different wavelengths of light. The focal length is dependent on the wavelength of light, so a change in the chromatic aberration means a change in the focal length.

When the target material 300 moves in an x-axial direction on a xy-plane, the radiation unit 100 may include a plurality of lenses arrayed on the xy-plane, so the rays of light transmitted onto the target material 300 via the respective lenses may have different chromatic aberrations along the x-axial direction of the lens array and the focal lengths of the rays of light may become different from each other due to the difference in the chromatic aberration. To this end, the radiation unit 100 may radiate rays of light having different chromatic aberrations to the respective lenses arrayed along the x-axial direction.

Due to the above-mentioned configuration, the rays of light radiated from the radiation unit 100 may form focal lengths gradually increasing in a z-axial direction as the positions of the focal points of the rays of light move to one side along the x-axial direction, for example, as shown in FIG. 1. In other words, the plurality of light focal points formed by the radiation unit 100 may have different coordinates in the z-axial direction.

When the target material 300 is exposed to an environment with the plurality of light focal points formed by the radiation unit 100, the apparatus for inspecting curvature of this invention can inspect the curvature or the bending of the surface of the target material 300. This inspection may be performed by the inspection unit 200.

The inspection unit 200 may inspect the curvature of the surface of the target material 300 using rays of light reflected from the target material 300. When the rays of light radiated from the radiation unit 100 reflect from the target material 300 and the reflected rays of light are transmitted to a predetermined position, an image may be reproduced on the position. Here, it is possible to determine whether the transmitted rays of light are in complete focus or not by analyzing the image. When it is determined that the transmitted rays of light are in complete focus, the focal length may become a distance between the radiation unit 100 and the target material 300. Here, because the radiation unit 100 forms the plurality of light focal points having different focal lengths in the z-axial direction, one focus $f_1$ of the focal points is formed on the surface of the target material 300. Here, it is required to previously set the focal lengths such that the focal lengths are within an expected curvature range of the target material 300. Described in detail, when the inspection unit 200 determines that a focus $f_1$ of a ray of light radiated from the radiation unit 100 is formed on the surface of the target material 300, the inspection unit 200 determines that the focal length of the focus $f_1$ is equal to the distance between the radiation unit 100 and the target material 300. Further, the inspection unit 200 can determine the curvature of the surface of the target material 300 by using distances determined using the focal lengths of the rays of light. When the distances determined by the inspection unit 200 are equal to each other over the whole area of the surface of the target material 300, the inspection unit 200 determines that the surface of the target material 300 is a flat surface having no curvature. However, when the distances determined by the inspection unit 200 are different from each other, the inspection unit 200 determines that the surface of the target material 300 is a curved surface having a curvature. Here, the curved portion on the surface of the target material 300 may be determined by determining coordinates of a portion having a distance different from the other distances.

Accordingly, to perform the inspection with high accuracy by the inspection unit 200, it is required to determine a portion on the surface of the target material 300 on which the focus is formed. In the present invention, it is assumed that the portion on the surface of the target material 300 on which the focus is formed is determined by a separate unit.

Figure 2:
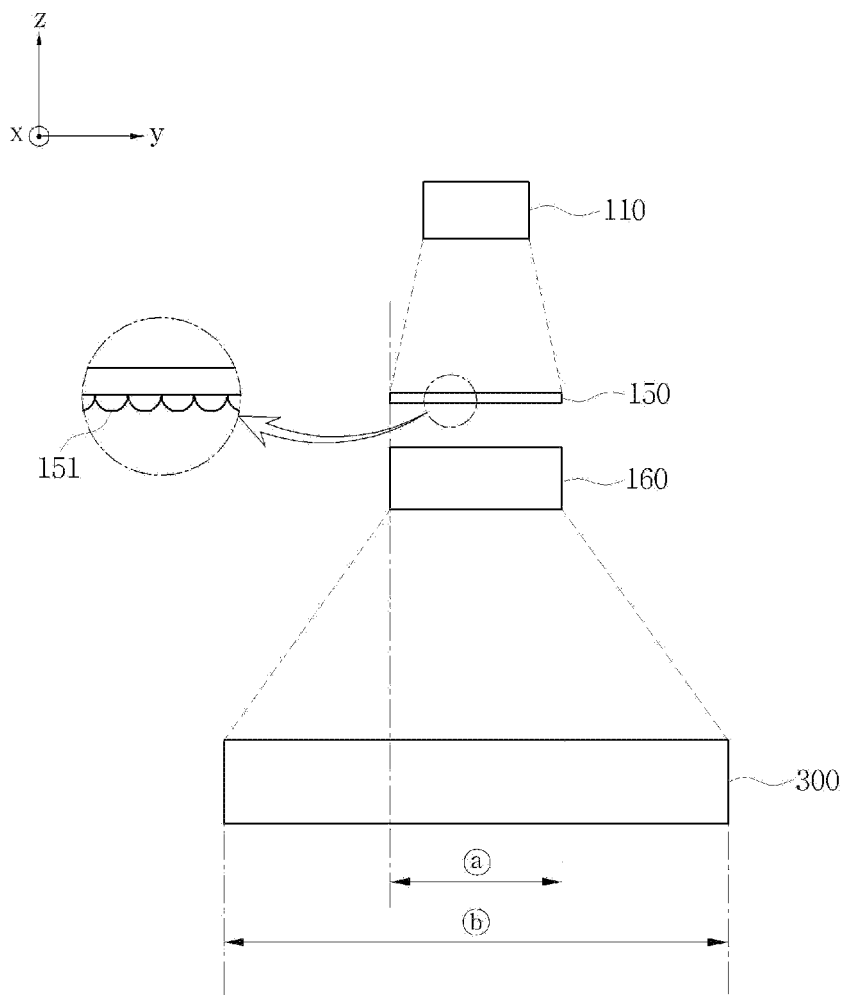
FIG. 2 is a view schematically illustrating a radiation unit constituting the apparatus for inspecting curvature according to the present invention.
Figure 3:
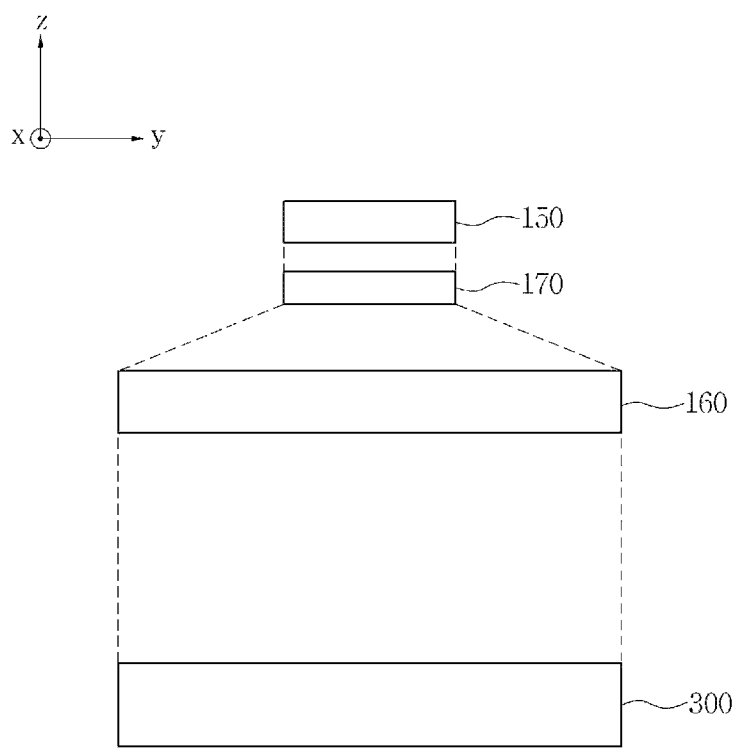
FIG. 3 is a view schematically illustrating a modification of the radiation unit constituting the apparatus for inspecting curvature according to the present invention.

FIG. 2 is a view schematically illustrating the radiation unit 100 constituting the apparatus for inspecting curvature according to the present invention. FIG. 3 is a view schematically illustrating a modification of the radiation unit 100 constituting the apparatus for inspecting curvature according to the present invention.

The radiation unit 100 may include: a light source 110 producing light; and an MLA (Micro Lens Array) 150 that forms a plurality of light focal points on different positions in a direction toward the target material 300.

The MLA 150 is a unit provided with a plurality of micro lenses 151, in which light is received via an input side and a plurality of light focal points are formed by the micro lenses 151 provided in an output side. To expand a first area in which the focal points formed by the MLA 150 are formed, an expansion lens 160 may be used. When an y-axial length of the first area (the width of the first area) is equal to or greater than an y-axial length of the target material 300 (the width of the target material 300) with the target material 300 moving in the x-axial direction as shown in FIG. 1, the radiation unit 100 may not move in an y-axial direction while scanning the target material 300. However, the width of the first area may be shorter than the width of the target material 300 according to the size of the target material 300.

The expansion lens 160 may expand the area formed by the focal points of the rays of light output from the MLA 150 to a second area that is larger than the planar first area of the MLA 150. In this case, the width of the second area may be equal to or greater than the width of the target material 300.

In FIG. 2, the width ⓐ of the first area is shorter than the width ⓑ of the target material 300. To inspect the target material 300 using the width ⓐ of the first area, the target material 300 and the radiation unit 100 are required to move relative to each other in the x-axial direction and in y-axial direction. However, when the expansion lens 160 is placed between the MLA 150 and the target material 300, the size of the first area, particularly, the width ⓐ of the first area can be expanded to be equal to or greater than the width ⓑ of the target material 300. In FIG. 2, the width of the second area is equal to the width of the target material 300.

The expansion lens 160 may be formed using a variety of lenses. For example, the expansion lens 160 may include a telecentric lens. When the expansion lens 160 is formed using the telecentric lens, the optical axis extending from the target material 300 to the expansion lens 160 may be a rectilinear axis and the apparatus of inspecting curvature may be used to inspect target materials regardless of stepped portions or angles of the materials while disregarding perspective values.

The telecentric lens may be configured to agree with the size of the second area, so the expansion lens 160 may include a subsidiary lens 170 that is placed between the MLA 150 and the telecentric lens of the expansion lens 160. Here, the expansion lens 160 expands the light having a size equal to that of the first area output from the MLA 150 to a size agreeable with the input side of the telecentric lens.

Figure 4:
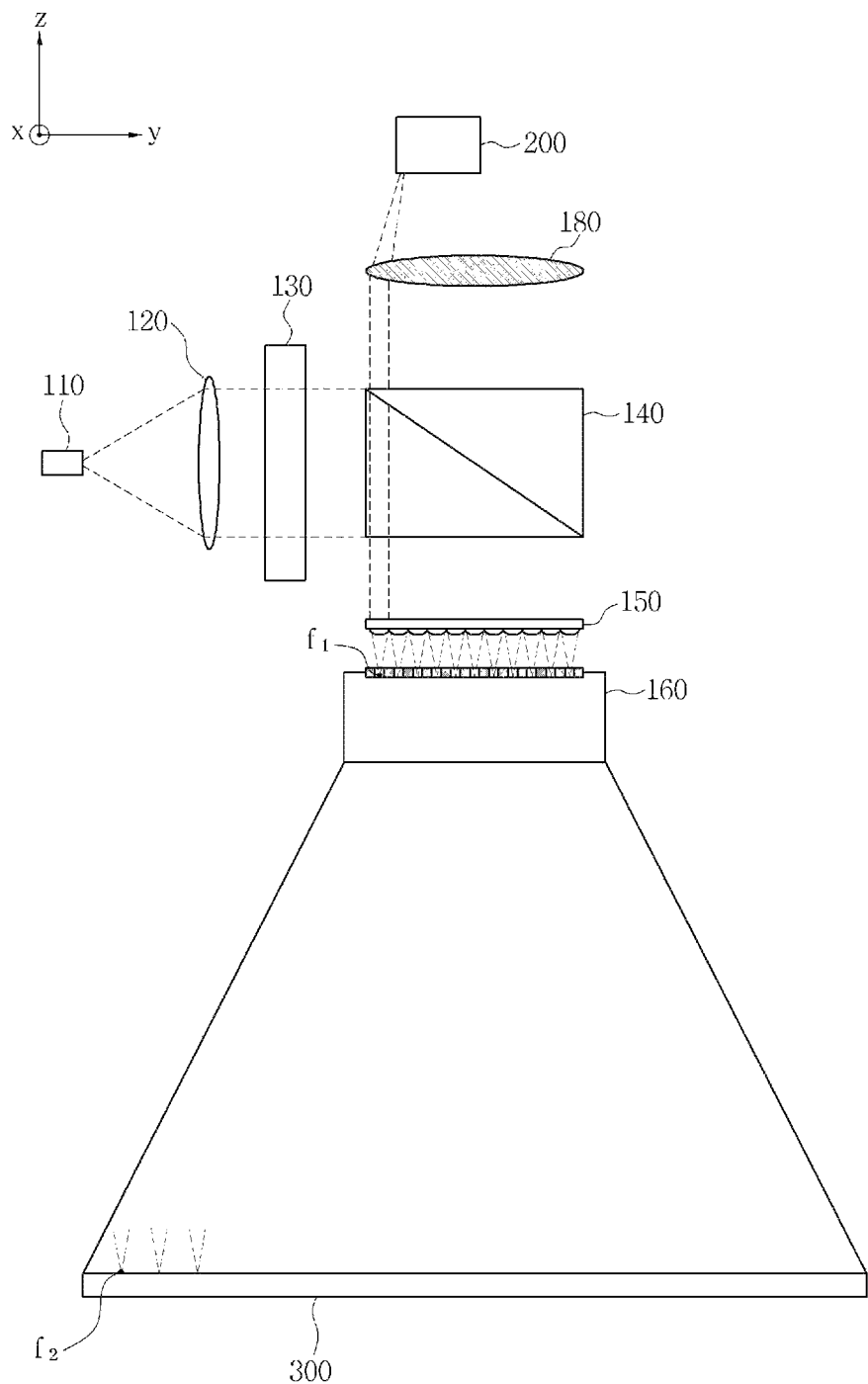
FIG. 4 is a view schematically illustrating an apparatus for inspecting curvature according to another embodiment of the present invention.

FIG. 4 is a view schematically illustrating an apparatus for inspecting curvature according to another embodiment of the present invention.

The apparatus for inspecting curvature shown in FIG. 4 may include a light source 110, a first lens unit 120, a spectral unit 130, a path changing unit 140 and a second lens unit.

Here, the light source 110 may produce multi-wavelength light, such as fine rays of light having various wavelengths. For example, the light source 110 may produce white light.

The first lens unit 120 may change the path of white light radially emitted from the light source 110 into a rectilinear path. The light of the light source 110 is emitted in radial directions due to the characteristics of the light and has a radial projection angle. The first lens unit 120 transmits the light of the light source 110 along a rectilinear path, so the light can be efficiently used.

The spectral unit 130 can change the white light output from the first lens unit 120 into a plurality of fine rays of light having different chromatic aberrations prior to outputting the fine rays of light. To this end, the spectral unit 130 may include a prism.

The path changing unit 140 can transmit the fine rays of light to different positions in the x-axial direction on the xy-plane. The path changing unit 140 may form the above-mentioned first area by transmitting the fine rays of light on the xy-plane. In other words, the path changing unit 140 can transmit the rays of light in surfaces. Here, the chromatic aberrations of the fine rays of light transmitted to x, y positions having the same x-axial coordinates may be equal to each other. For example, when fine rays of light have $x_1 \sim x_5$ coordinates on the x-axis and $y_1 \sim y_{17}$ coordinates on the y-axis, the fine rays of light having $x_1$, $y_1 \sim x_1$, $y_{17}$ coordinates may have the same chromatic aberrations.

The second lens unit may form the focal points of the respective fine rays of light and may move in the x-axial direction relative to the target material 300 placed on the xy-plane. The second lens unit may include the above-mentioned MLA 150. The area formed by the focal points of the rays of light output from the second lens unit becomes the above-mentioned first area and this first area may be equal to the area of the rays of light output from the path changing unit 140.

A third lens unit may be placed between the second lens unit and the target material 300. The third lens unit may increase the distances between the focal points formed by the second lens unit on the xy-plane. The third lens unit may include the above-mentioned expansion lens 160.

Figure 5:
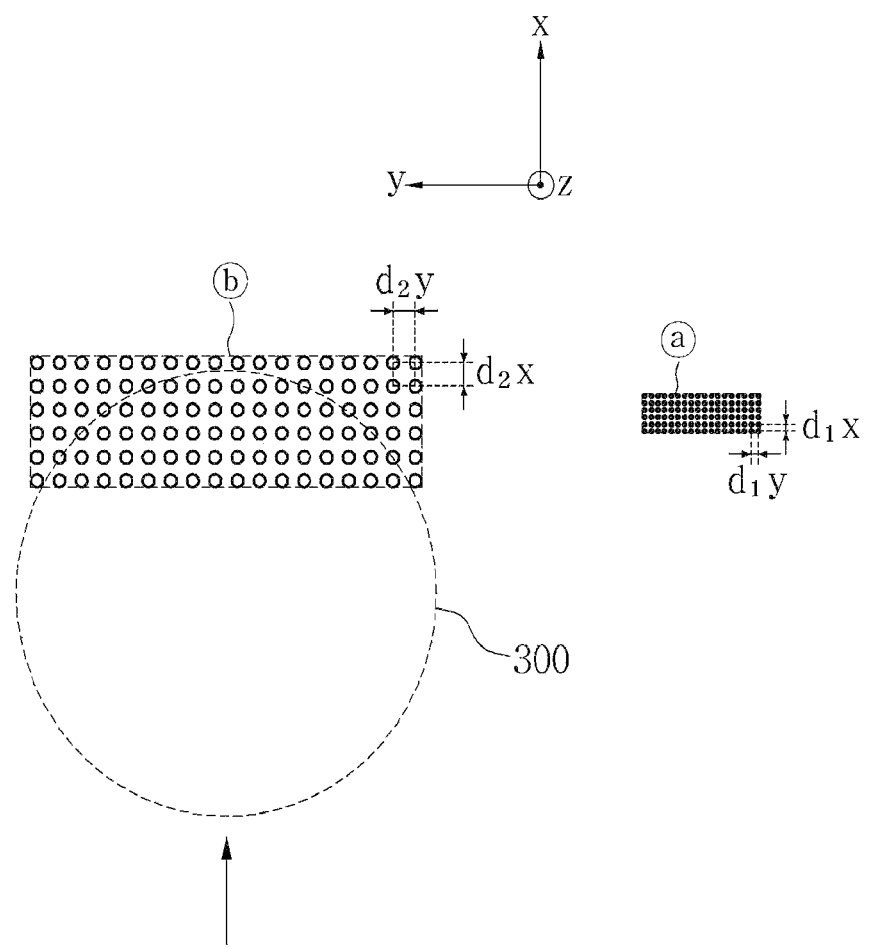
FIG. 5 is a view schematically illustrating an area formed by the focal points of fine rays of light radiated onto a target material by the apparatus for inspecting curvature of the present invention.

FIG. 5 is a view schematically illustrating the area formed by the focal points of the fine rays of light radiated onto the target material 300 by the apparatus for inspecting curvature of the present invention.

As show in FIG. 5, it is noted that the distances $d2x$, $d2y$ between the focal points formed in the second area ⓑ are greater than the distances $d1x$, $d1y$ between the focal points formed in the first area ⓐ. Accordingly, the coordinates of the focus $f_1$ formed by the second lens unit and the coordinates of the focus $f_2$ formed by the third lens unit may be different from each other. Further, the surface area of the second area may be larger than the surface are of the first area. In this case, the size of the second area may be determined according to the width of the target material 300. Here, because the third lens unit increases the distances between the focal points, the resolving power may be reduced. However, this problem may be easily and simply solved by increasing the resolving power of the second lens unit or by forming more focal points. Thus, it is required to appropriately increase the number of fine rays of light.

Return to FIG. 4, the apparatus for inspecting curvature may include the inspection unit 200.

The inspection unit 200 may determine the distance between the path changing unit 140 or the second lens unit and the surface of the target material 300 by using rays of light reflected from the target material 300. Further, the inspection unit 200 may determine the curvature of the surface of the target material 300 using the distances.

The path changing unit 140 may receive the rays of light reflected from the target material 300 and may transmit the rays of light to the inspection unit 200. In this case, the path changing unit 140 may be an optical device that can output incident light received from a first direction to a second direction, in which the first direction may be a direction from the light source 110, and can output incident light received from the second direction to a third direction, in which the second direction may be a direction from the target material 300.

Further, a projection lens 180 may be placed between the path changing unit 140 and the inspection unit 200. The projection lens 180 may project the light output from the path changing unit 140 onto the inspection unit 200.

As described above, the apparatus for inspecting curvature of the present invention can inspect the curvature of a surface of an target material 300 by forming focal points having different coordinates in a z-axial direction using the chromatic aberration and by moving the target material 300 within the range of the focal points in the z-axial direction, and by determining the focal length of a focus formed on the surface of the target material 300.

In other words, the apparatus for inspecting curvature of the present invention can form a plurality of light focal points having different focal lengths using fine rays of light having different chromatic aberrations.

The apparatus for inspecting curvature of this invention can inspect the curvature or the bending of the surface of the target material 300 at low cost, at a high speed and with high accuracy.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An apparatus for inspecting curvature, comprising:
    a radiation source configured to radiate rays of light;
    a plurality of lenses comprising different chromatic aberrations configured to project the rays of light at different local lengths onto a surface of a target material; and
    an inspector configured to determine a curvature of the surface based on detecting the rays of the light reflected from the target material,
    wherein the rays of light transmitted by the respective lenses have different chromatic aberrations, and the different focal lengths are formed due to the difference in chromatic aberrations.

2. The apparatus for inspecting curvature of claim 1, wherein:
    the target material is configured to move in an x-axial direction on a xy-plane,
    the plurality of lenses are arrayed on the xy-plane, and
    the chromatic aberrations are arranged along the x-axial direction of the lens array.

3. The apparatus for inspecting curvature of claim 1, wherein the radiation source comprises:
    a light source configured to emit the rays of light;
    a micro lens array configured to project focal points of the rays of light toward the target material; and
    an expansion lens configured to expand the rays of light projected from the micro lens array to a first area that is larger than a planar second area of the micro lens array.

4. An apparatus for inspecting curvature, comprising:
    a light source configured to produce white light;
    a first lens configured to change a path of the white light radially emitted from the light source into a rectilinear path;
    a spectral converter configured to convert the white light output from the first lens unit into a plurality of fine rays of light having different chromatic aberrations and to output the fine rays of light;
    a path changer configured to transmit the rays of light to different positions in an x-axial direction on a xy-plane;
    a second lens unit comprising a micro lens array configured to form focal points of the rays of light and to move in the x-axial direction relative to a target material placed on the xy-plane; and
    a third lens positioned between the second lens and the target material and configured to increase distances between the light focal points formed by the second lens the xy-plane.

* * * * *